June 15, 1937. R. C. MURPHEY Plant Pat. 251

CHRYSANTHEMUM

Filed Dec. 5, 1936

Inventor

ROBERT C. MURPHEY.

By Robert Robb

Attorneys

Patented June 15, 1937

UNITED STATES PATENT OFFICE

251

CHRYSANTHEMUM

Robert C. Murphey, Urbana, Ohio, assignor to
R. H. Murphey's Sons Company, Urbana, Ohio Application December 5, 1936, Serial No. 114,504

1 Claim. (Cl. 47—60)

My new variety of chrysanthemum plant is of the type wherein the habit of growth of the plant is spheroidal or mound-like, the outer surface of the plant when in bloom being completely covered with flowers.

This type of chrysanthemum plant, being a profuse bloomer yet dwarf and compact, makes an ideal plant for border and group planting. Its effectiveness when so planted results from the profusion of blooms growing close together in such a manner as to present solid masses of vivid color. In addition to its value in border and group planting, my new variety is also valuable as a pot plant.

Its novelty resides particularly in the production of a chrysanthemum plant having the characteristics above set forth, the flowers of which have a distinctive yellow color, though other novel features will become apparent as the description progresses.

My new variety of chrysanthemum was produced by hybridizing. It was originated by crossing an Ohio State chrysanthemum with a pink chrysanthemum known as Pink Azaleamum, being a seedling of the two parents named.

My new variety resembles the parent Pink Azaleamum in its habits of growth, its foliage, and the shape of its buds and flowers, but the foliage of my new variety is less serrated than the foliage of Pink Azaleamum. The flowers of my new variety resemble the Ohio State chrysanthemum in their color, and the plant also exhibits occasional shoots which resemble the foliage of this latter parent variety.

The particular habits of growth of my new variety which resemble those of the parent Pink Azaleamum are the characteristics of dwarfness and compactness, the spheroidal or mound-like form of the plant, and the characteristic of the plant in completely covering its outer surface with a multitude of blooms.

Another distinctive feature of my new variety is its early blooming habit. The blooming time for terminal buds is about September 10th, in the region of Urbana, Ohio, and the lateral buds bloom ten days to two weeks later. The above dates are of the natural blooming time, with no artificial aid being given to hasten the blooming time. The length of the blooming period is not at the present time known but it is believed to be considerably longer than five weeks, which is the length of time plants have been out in bloom before being prematurely halted by unusual weather conditions.

The plants of my new variety grow as large as three to four feet across, and their usual height is about eighteen inches, in the region of Urbana, Ohio.

My new variety of chrysanthemum plant has been found to hold its distinguishing characteristics through succeeding generations by means of a sexual reproduction, propagation being carried on from cuttings.

Figure 1:
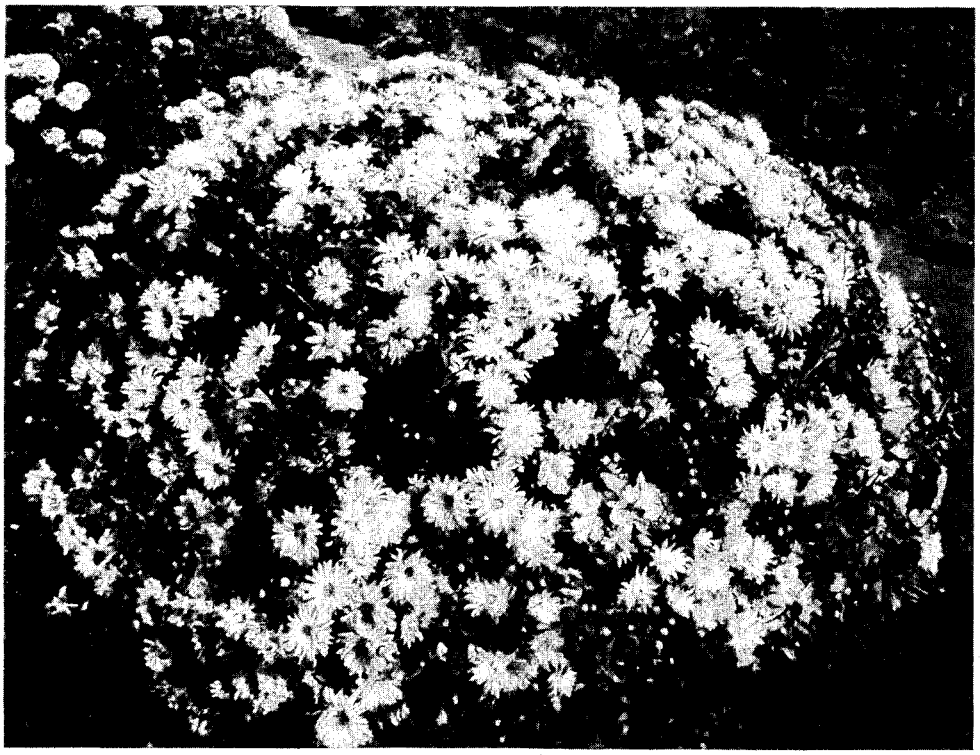
Figure 1 is a view of one of the plants of my new variety, showing the spheroidal or mound-like form of the plant.
Figure 2:
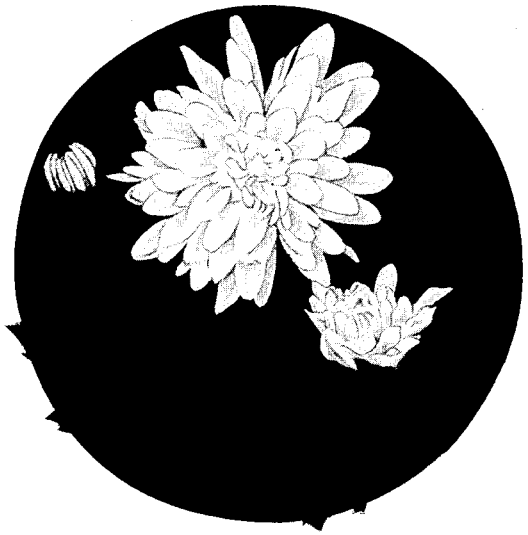
Figure 2 shows details of a single flower, a bud, and a bud just opening.

The following detailed description was made from a plant grown outdoors in alkaline soil without chemicals.

*Description*

*Type:*

Hardy; dwarf; outdoors; seedling; for garden decoration or pot plant.

*Flower:*

*Locality where grown.*—Urbana, Ohio,

*Flowers borne.*—Many to stem; in cluster; on medium stems.

*Quantity of bloom.*—Abundant; outdoors.

*Continuity.*—Continuous.

*Bud:*

*Before calyx breaks.—Size*—medium. *Form*—globular.

*As calyx breaks.—Color*—yellow.

*As first petal opens.—Size*—medium. *Form*—globular. *Color*—yellow. *Opening*—opens up well.

*Bloom:*

*Size when fully open.*—Medium, one inch to one-and-one-half inches.

*Petalage.*—Semi-double; arranged regularly.

*Form.*—Flat.

*Petals:*

Soft.

*Shape.*—Oval.

*Color:*

Compared with Maerz & Paul Dictionary of Color Tables. *Outside surface.*—Yellow of Plate 10-K-2, overlaid with red of Plate 3-L-2, especially at base of petals.

*Inside surface.*—Yellow of Plate 10-L-1 overlaid less distinctly than the outside surface with red of Plate 3-L-2.

*Plant:*

*Foliage.*—Abundant, medium, heavy.

*Color.*—Upper surface—normal green; under surface—light green.

*Disease.*—Resistant to mildew, blackspot.

*Growth:*

Dwarf, bushy, vigorous.

I claim:

A new and distinct variety of chrysanthemum plant as herein shown and described, characterized by its many-flowered and spheroidal habit of growth, its early blooming period, and the yellow color of its flower.

ROBERT C. MURPHEY.